United States Patent
Bettex

[11] 3,946,728
[45] Mar. 30, 1976

[54] SURGICAL DEVICE

[75] Inventor: Marcel Bettex, Bern, Switzerland

[73] Assignee: Protek A.G., Switzerland

[22] Filed: May 24, 1974

[21] Appl. No.: 473,238

[30] Foreign Application Priority Data
May 15, 1974 Switzerland............................ 7633/74
June 17, 1974 Switzerland............................ 6626/74

[52] U.S. Cl. ................................. 128/69; 128/20
[51] Int. Cl.² ............................................ A61F 5/00
[58] Field of Search ........... 128/69, 68, 83, 346, 92, 128/20; 24/16 PB, 22, 23, 25, 206 A, 206 R, 30.5 P, 30.5 L, 201 S, 201 R

[56] References Cited
UNITED STATES PATENTS

| | | | |
|---|---|---|---|
| 204,764 | 6/1878 | Rutherford et al. | 24/22 |
| 2,344,631 | 3/1944 | Paley et al. | 128/83 |
| 2,860,393 | 11/1958 | Brock | 24/25 X |
| 3,469,573 | 9/1969 | Florio | 128/92 R |
| 3,522,799 | 8/1970 | Gauthier | 128/20 |
| 3,576,054 | 4/1971 | Rynk | 128/346 X |
| 3,653,099 | 4/1972 | Hoffman | 24/16 PB |
| 3,667,471 | 6/1972 | Doty et al. | 128/346 X |
| 3,687,131 | 8/1972 | Rayport et al. | 128/346 X |

*Primary Examiner*—John D. Yasko
*Attorney, Agent, or Firm*—McGlew and Tuttle

[57] ABSTRACT

A device for use in the surgical treatment of a patient suffering from a funnel breast condition is disclosed. The device comprises two mutually symmetrical clamping members each having an end portion adapted to be secured to a respective rib of such a patient, fastening means for rigidly connecting to one another the respective other end portions of the two clamping members, and a flexible member engageable with the fastening means and adapted to attach the latter to the breast bone of such patient.

6 Claims, 18 Drawing Figures

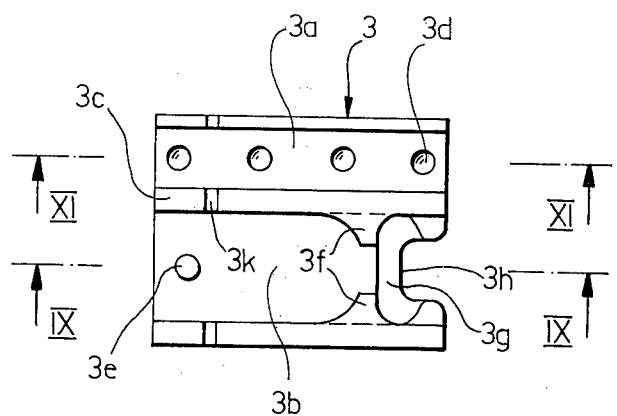
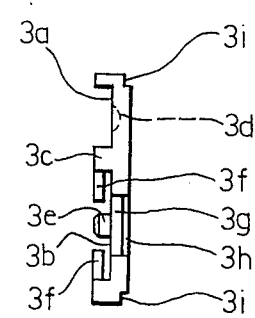
Fig. 5  Fig. 6
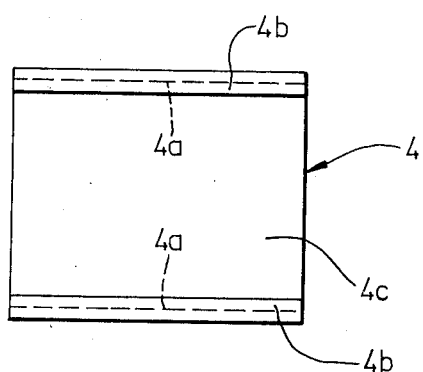
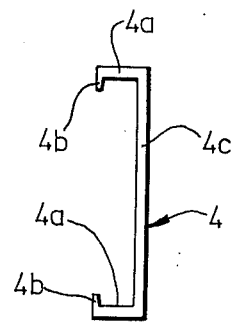
Fig. 7  Fig. 8

SURGICAL DEVICE

BACKGROUND OF THE INVENTION

The present invention relates to a device for use in the surgical treatment of a patient suffering from a funnel breast condition.

Until now, one has corrected the deficiency - typical for a so-called funnel breast condition - of the breast bone and of the ribs separating several pairs of ribs from the breast bone, fixing metallic clamps on to them, and securing the two clamps corresponding to each pair of ribs, on the one hand, to one another and, on the other hand, to the breast bone. Since previously one always employed only smooth clamps, and used wire for the connection of the same, the strength of the connection was not very high. The clamps could loosen themselves and be displaced relative to one another. For the securing of the clamps on the breast bone, one was forced to bore through the latter and to pass a wire through the bone. Moreover, the clamps might still be rotatably displaceable about their longitudinal axis. Indeed, the ends of the wire serving for the connection have been known to penetrate through the skin. It has also been found that pieces of such wire sometimes break off and begin to move along the ribs. A further disadvantage of the previous method of correction was that, in order to remove the clamps, it was often necessary to expose a relatively large area of the breast bone and the parts surrounding it to enable a surgeon to remove all such wires. Seen as a whole, the conventional method for the correction of a funnel breast is still subject to many disadvantages and therefore worthy of improvement.

SUMMARY OF THE INVENTION

According to the present invention, there is provided a device for use in the surgical treatment of a patient suffering from a funnel breast condition, the device comprising two mutually symmetrical clamping members each having an end portion adapted to be secured to a respective rib of such a patient, fastening means for substantially rigidly connecting to one another the respective other end portions of the two clamping members, and a fastening element engageable with the fastening means and adapted to attach the latter to the breast bone of such a patient.

Preferably, each clamping member or clamp is substantially band-shaped and is provided with a plurality of equally spaced depressions disposed rectilinearly one behind the other in the longitudinal direction on one surface of the clamp and, on the other surface is provided with a plurality of protrusions, which are likewise disposed in a line one behind the other and which are disposed at the same spacing as the depressions to be complementary to the depressions, wherein the depressions and protrusions on each of the two clamps are of identical shape. The protrusions and depressions may each have a spherically shaped surface. It is advantageous if the fastening element is in the form of a tension band which is provided with a plurality of apertures disposed one behind the other in longitudinal direction and if one of its end portions is provided with anchoring means for the releasably attaching of the flexible strip member to the fastening means. The fastening means may comprise a base plate and a cover plate releasably connected with the latter, wherein the base plate defines a first guide groove of U-shaped cross-section to receive the two clamps and a second guide groove to receive the tension band. The floor or inner base surface of the first guide groove is provided with depressions, which are disposed in a straight line and which correspond to the protrusions of the clamps, and the depth of the groove corresponds to twice the thickness of each clamp. One end portion of the second guide groove is provided with a spigot, which projects out of the floor or inner base surface of the second groove and which is adapted to be engageable with the apertures of the tension band, the respective other end portion of the second groove being provided with engagement means to co-operate with the anchoring means of the tension band, a portion of the second groove intermediate its end portions being provided with projections which project inwardly from the groove side wall and which define a channel having depth corresponding to the tension band thickness between mutually facing surfaces of the projections and the groove floor, the two guide grooves each being closed off by the cover plate when the latter is connected to the base plate. The cover plate is preferably constructed as a guide channel, into which the base plate can be pushed.

To facilitate securing of the tension band to the fastening means, the base plate is provided with a transverse groove, which extends perpendicularly to the two guide grooves and which is disposed in the direct vicinity of the spigot, and serves as abutment for a pin provided as an assembly expedient during the connection of the fastening means with the tension band.

All parts of the device may consist of metal or of a suitable synthetic material.

BRIEF DESCRIPTION OF THE DRAWINGS

Embodiments of the invention will now be more particularly described with reference to the accompanying drawings, in which:-

FIG. 5 shows a base plate in plan view;
FIG. 6 shows a side elevation of the base plate;
FIG. 7 shows a cover plate in bottom view;
FIG. 8 shows a side elevational view of the plate shown in FIG. 7.

DESCRIPTION OF THE PREFERRED EMBODIMENTS

Figure 1:
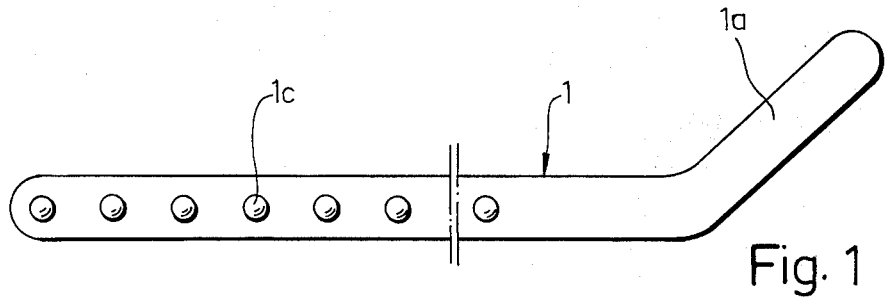
FIG. 1 shows a plan view of a clamp.
Figure 2:
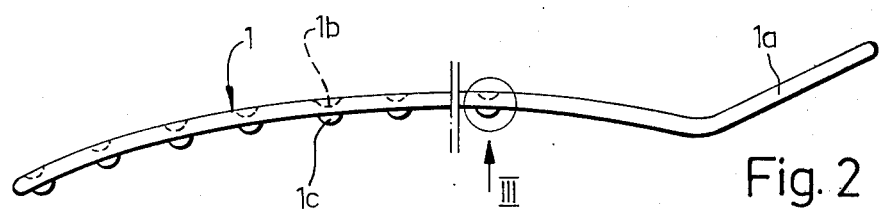
FIG. 2 shows a side view of the clamp shown in FIG. 1.
Figure 3:
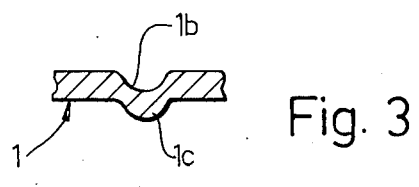
FIG. 3 shows a detail of FIG. 2, in section.

FIG. 1 shows a right hand clamping member or clamp 1. The clamp consists of a metal strip, one end portion 1a of which is bent out of the general longitudinal direction of the strip. The clamp displays a slight curvature, with the mentioned end portion 1a again being bent over through approximately 45° against the general curvature. FIGS. 1 and 2 show this clearly. The longer, "straight" part of the clamp displays on its convex surface a series of depressions 1b, which are equally spaced from one another and disposed rectilinearly one behind the other. On the opposite surface, the clamp displays, exactly at the positions of the depressions 1b, protrusions 1c, the shape of which corresponds exactly to that of the depressions 1b. The surfaces of the depressions and of the protrusions are each spherically shaped, but they could just as well also be constructed otherwise. FIG. 3 shows such a depression and protrusion disposed opposite to it.

The left hand clamp is constructed completely symmetrically with the right hand clamp, for which reason it is not separately represented in the drawing.

Figure 4:
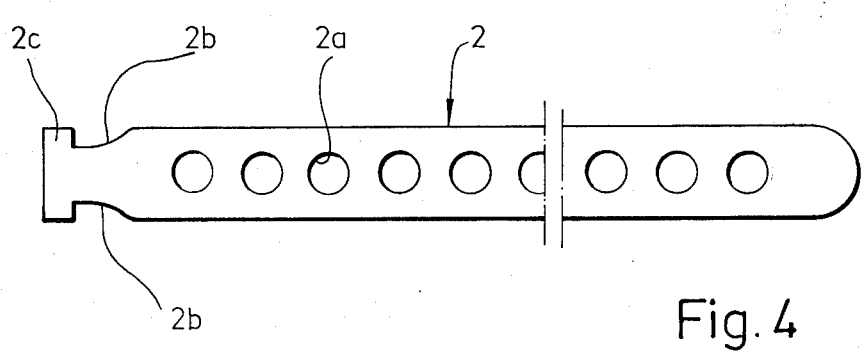
FIG. 4 shows a tension band.

FIG. 4 shows a flexible strip member or tension band 2. The band 2 is in the form of a thin, flexible metal strip and is provided with apertures 2a, which are disposed to be equally spaced in a straight line one behind the other and which all have the same diameter. One end portion of the tension band 2 is provided with anchoring means, which enables it to be fastened to the yet to be described fastening means. For this, the band end is provided with two lateral recesses 2b, which are so constructed, that the outermost band end 2c forms with the remainder of the band a T, the cross beam 2c of which serves to engage in a recess in the fastening means.

FIG. 5 shows a plan view of a base plate 3. This is provided with two parallel guide grooves 3a and 3b, which are each substantially U-shaped in cross-section and which are separated by a common wall 3c. The guide groove 3a is of such width that a clamp can be inserted into it, without it jamming. The guide groove 3b has a width slightly greater than that of the tension band 2, so that the latter can be inserted easily into it.

The guide groove 3a displays in its floor equidistant depressions 3d, which are disposed rectilinearly one behind the other and which are constructed completely similarly to those of the clamps 1.

The guide groove 3b possesses in one of its end portions a cylindrical spigot 3e, which projects out of its floor and the diameter of which is slightly smaller than the diameter of the apertures and in the tension band. After about three quarters of the groove length, reckoned from the spigot-side end, two projections 3f project out of the groove side walls, parallel to the groove floor, into the groove, and leave open between them and the groove floor a channel of which the cross-section is only slightly greater than that of the tension band. Immediately after these projections, the groove floor displays a depression 3g in the form of an oval extending transversely to the groove. The length of the oval corresponds to the width of the guide groove, while the depth of the oval corresponds to the thickness of the transverse web 2c of the tension band.

The last part of the groove floor is provided with a recess 3h, which is open towards the groove end. The width of the recess 3h corresponds to the width of the part of the tension band 2 narrowed by the recesses 2b.

As FIG. 6 shows, the base plate at its under surface is provided, on each side, with a longitudinal groove 3i, which extends at the edge and which serves for the securing of the cover plate 4 represented in FIGS. 7 and 8. The latter consists substantially of a profile rail U-shaped in cross-section, yet in each case a rib 4b projects from the edges of its limbs 4a perpendicularly to the limbs into the interior space of the U. The cover plate 4 is so dimensioned that it can be slidably pushed fully over the base plate 3, the ribs 4b engaging in the longitudinal grooves 3i and the floor 4c of the cover plate 4 closing off the guide grooves 3a and 3b of the base plate, in that it rests on the edges of the groove side walls.

Figure 9:
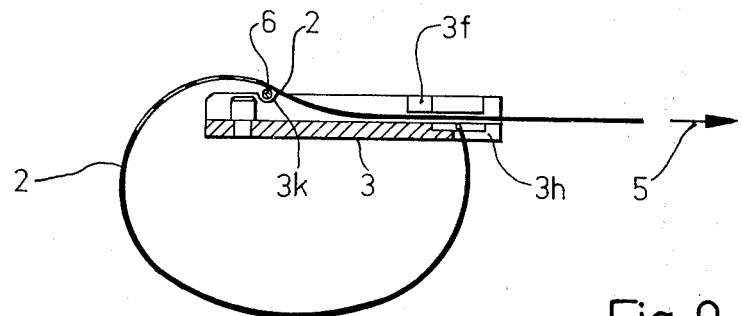
FIG. 9 shows a section on the line IX—IX in FIG. 5, but with inserted tension band.
Figure 10:
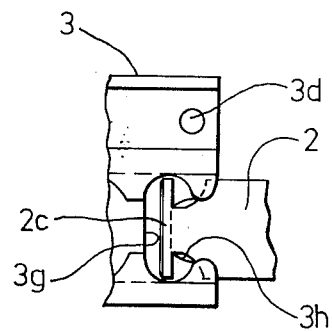
FIG. 10 shows a sketch for the illustration of the mode of operation of the anchoring means.

FIGS. 9 and 10 show how the tension band 2 is connected with the fastening means, of which only the base plate 3 is represented here. The T-shaped end 2c of the tension band 2 is inserted through the recess 3h into the guide groove 3b, and there engaged in the oval depression 3g, as in particular FIG. 10 illustrates. Thereupon one forms a loop and inserts the other end of the tension band into the guide groove 3b in such a manner that, on the one hand it runs through under the projections 3f and on the other hand however it leads away by its other, T-shaped end. By pulling in direction of the arrow 5, the size of the loop can now be varied.

By reason of the elastically resilient properties of the tension band, the latter during the drawing together of the loop endeavours, by one of its apertures 2a, to engage at the spigot 3e, which sometimes can act interferingly. For the simpler and more convenient fixing of the tension band to the fastening means, a pin 6 is provided which - during the drawing together of the tension band loop - can be inserted as an assembly expedient into a transverse groove 3k extending transversely to the guide grooves 3a and 3b in the direct vicinity of the spigot 3e, as shown in FIG. 9. When the loop has the desired size, the pin 6 is removed and the spigot 3e can engage in one of the apertures 2a of the tension band, whereby the latter is securely connected with the fastening means.

Figure 11:
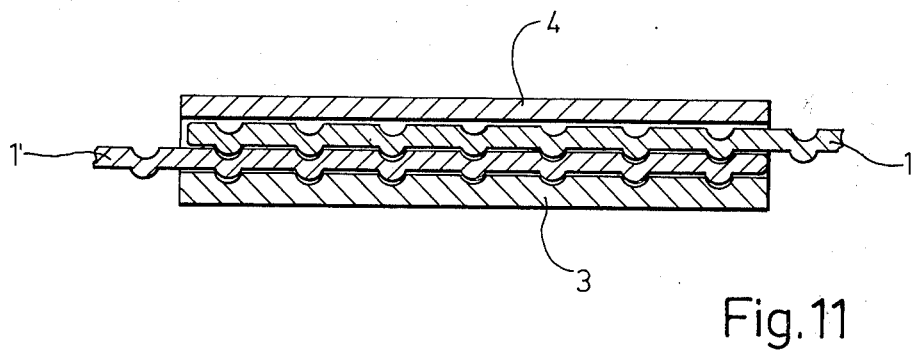
FIG. 11 shows a section according to the line XI—XI of FIG. 5, but with inserted clamps.
Figure 12:
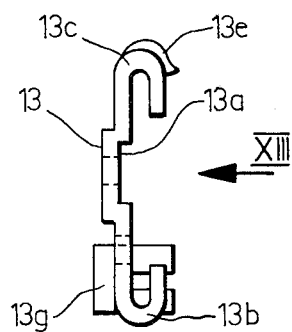
FIG. 12 shows a side elevation view of another construction of a base plate.
Figure 13:
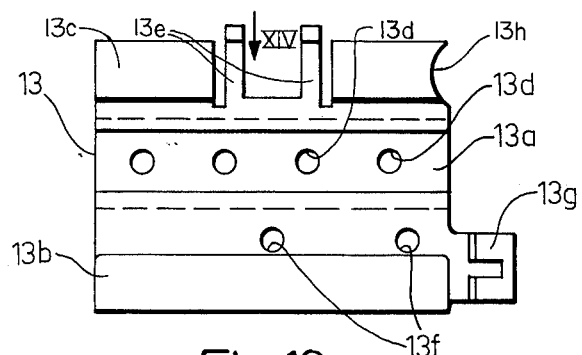
FIG. 13 shows a view in the viewing direction indicated in FIG. 12 by the arrow XIII.
Figure 14:
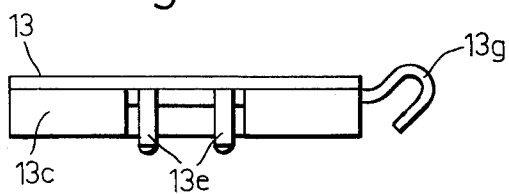
FIG. 14 shows a view in the viewing direction indicated in FIG. 13 by the arrow XIV.
Figure 15:
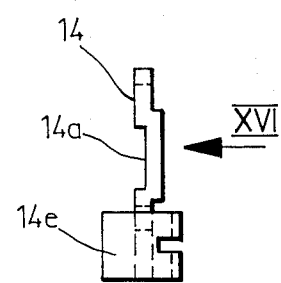
FIG. 15 shows a side elevation of the cover plate forming the counterpart to the base plate shown in FIGS. 12 to 14.
Figure 16:
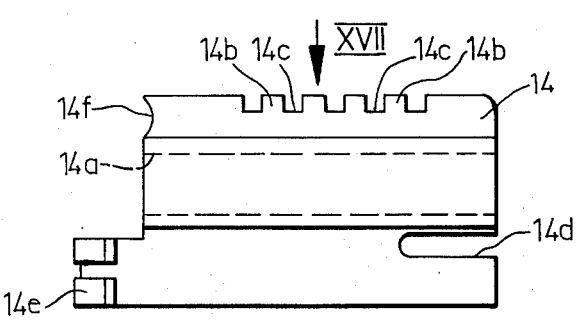
FIG. 16 shows a view in the viewing direction indicated in FIG. 15 by the arrow XVI.
Figure 17:
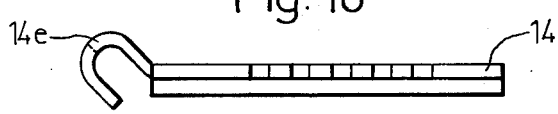
FIG. 17 shows a view in the viewing direction indicated in FIG. 16 by the arrow XVII.
Figure 18:
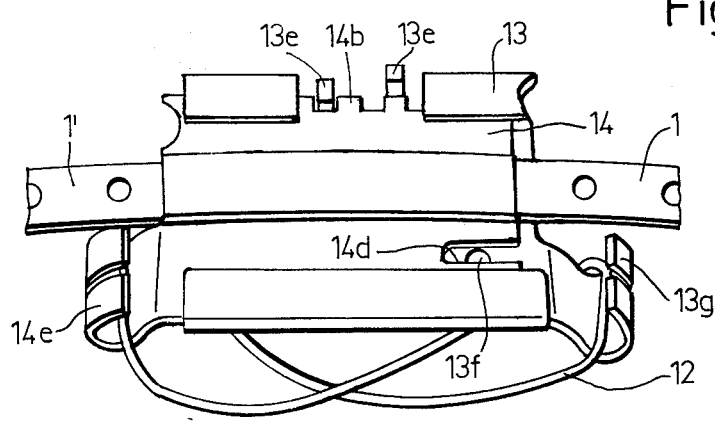
FIG. 18 shows an axonometric illustration of a fastening formed by the plates illustrated in FIGS. 12 to 17.

The securing of the right-hand clamp 1 to the left-hand clamp 1' (see FIG. 11) ensues by simple superposition and insertion into the guide groove 3a of the base plate 3, as FIG. 11 shows. In this, in each case the protrusions of the clamp disposed thereabove engage in the depressions of the clamp disposed therebelow, and the latter's protrusions engage in the depressions in the groove floor. Now the cover plate 4 is pushed over the base plate 3, whereby the fastening means is now closed and neither the clamps nor the tension band can loosen or be released.

For the correction of the breast bone deficiency, one now proceeds in the following way: Initially one inserts into each of the separated pairs of ribs a respective left hand or right hand clamp, by the angled over end. Hereupon, one fixes the fastening in the described manner at the tension band, the tension band loop being guided around the breast bone. By drawing together of the loop, the base plate of the fastening means can be substantially rigidly secured to the breast bone. During this process use can be made of the assembly aiding pin 6. After the fixing of the base plate 3 to the breast bone, the clamps are inserted in the described manner into the guide groove 3a of the base plate 3. Any projecting portions of the clamps may now be cut off, as required. Finally, the cover plate is pushed on to the base plate, whereby all parts of the device as well as the breast bone and the ribs are securely connected with one another.

If it is desired to release the connection again, one needs only to proceed in the reverse sequence to that described above.

Shown in FIGS. 12 to 18 is a further example of embodiment of a fastening means, which likewise consists of a base plate 13 and a cover plate 14 releasably connected with the base plate 13. The base plate 13 displays a guide groove 13a, the breadth and depth of which is so dimensioned that one of the clamps 1,1" can be inserted in it and thereby be secured against rotation. The guide groove 13a is provided along its centre line with equidistant bores 13d. These are so dimensioned, that the protrusions of the inserted clamp 1,1" engage in them on the fastening means 13, 14 being closed, so that the clamp 1,1" is secured against longitudinal displacementS.

For the remainder, the base plate displays one limb 13b, 13c each on its long sides parallel to the guide groove 13a. These two limbs 13b, 13c are curved in such a manner that the base plate - as is evident from FIG. 12 - has a substantially C-shaped cross-section and thus forms a guide rail, into which the cover plate 14 can be pushed.

In its central section, the limb 13c displays an interruption, in which two plastically flexible tongues 13e are arranged. The base plate 13 further displays two further bores 13f. A hook 13g and a recess 13h of circular segment shape is further present on one side of the base plate 13. The cover plate 14 displays a guide groove 14a, which serves for guiding and retaining of one of the clamps 1 and the breadth and depth of which corresponds to the corresponding dimensions of the clamp 1 concerned. Furthermore, the cover plate 14 displays at one of its longitudinal edges a toothing, which is formed by teeth 14b and recesses 14 c disposed therebetween. The cover plate 14 is further provided with an elongate recess 14d, which extends parallel to the guide groove 14a. Additionally, it displays on one side a hook 14e and a recess 14f of circular segment shape.

For the fastening of the clamps 1,1", these are - as already described - taken apart and so inserted into the guide groove 13a of the base plate 13, that the protrusions of the one clamp 1" engage in the openings 13d. Consecutively, the cover plate 14 is pushed into the base plate 13, so that this gets into the position shown in FIG. 18. The upper clamp 1 is now secured against rotation by the guide groove 14a and is undisplaceably connected with the lower clamp 1". In order to enable the frictional force arising on the pushing in of the cover plate 14 to be overcome effortlessly, round pliers can perhaps be employed and their cheeks applied at the recesses 13h and 14f, respectively.

So that the cover plate 14 can no longer be displaced relative to the base plate 13, one of the tongues 13e can now be bent by pliers and notched into one of the recesses 14c. The spacing of the two tongues 13e is about half a tongue breadth greater than the spacing of two adjacent recesses, so that according to the respective position of the cover plate 14 relative to the base plate 13 either the one or the other tongue can be notched in. It is of course also possible to provide both longitudinal edges of the base or cover plate with tongues or recesses, so that in practically every position one of the tongues can be notched in.

When the fastening means 13, 14 is closed in this manner, it can be attached at the breast bone by means of a fastening element such as a loop of fastening wire 12, in which the two hooks 13g and 14e are hooked in. So that the hooks cannot cause any injuries, they are bent somewhat to the rear.

For the removal of the device, the fastening wire 12 is first cut or otherwise released, and removed. Consecutively, the notched-in tongue 13e is again bent outwardly, so that the two plates 13, 14 of the fastening means can again be displaced. The pushing apart of the two plates 13 and 14 can ensue with the aid of round pliers, one cheek point of which is introduced into one of the bores 13f and the other is applied at the inner end of the recess 14d at the cover plate and the cheeks of which are then spread apart.

The device embodying the invention for the surgical treatment of a funnel breast condition has the advantage that it permits a simple and convenient connection of the ribs and of the breast bone and that the clamps cannot tip or slide about their longitudinal axis. Beyond this, it is also of importance that an entry only very small according to area need be made for the removal of the clamps after the funnel breast condition has been corrected.

What is claimed is:

1. A device for use in the surgical treatment of a patient suffering from a funnel breast condition, the device comprising in combination: two mutually symmetrical clamping members each having an end portion adapted to be secured to a respective rib of such a patient; fastening means releasably rigidly connecting to one another the respective other end portions of said two clamping members; and a fastening element releasably engaging with said fastening means and adapted to attach the latter to the breast bone of such a patient; each clamping member comprising an elongate strip, one surface of said strip being provided with a plurality of depressions equally spaced in the longitudinal direction of the strip and the respective other surface of said strip being provided with a plurality of protrusions complementary with said depressions, said depressions and protrusions provided on said two clamping members being of identical shape; said fastening means comprising a base plate and a cover plate releasably connected to said base plate, said base plate defining a guide groove adapted to receive at least one of said clamping members, a portion of said base plate defining the floor of said groove being provided with a plurality of depressions which, upon said cover plate being connected to said base plate to close said fastening means, engage with said protrusions on a respective one of said clamping members disposed next adjacent said floor of said guide groove, said depressions on said one clamping member being engaged by said protrusions on the respective other said clamping member, which is being retained in engagement with said one clamping member by said cover plate.

2. A device as defined in claim 1, wherein said base plate is provided with a second guide groove of substantially U-shaped cross-section and adapted to receive said flexible strip member, said first mentioned guide groove having a depth substantially equal to twice the thickness of each of said clamping members, said base plate being provided with a spigot which projects out of the inner base surface of one end portion of said second guide groove and which is adapted to be engageable with said apertures in said flexible strip member, being provided in the respective other end portion of said second guide groove with engagement means for co-operating with said anchoring means of said flexible strip member, and being provided with projections which project inwardly from the side walls of an intermediate portion of said second guide groove to define between mutually facing surface portions of said base surface and said projections a channel having a depth substantially equal to the thickness of said flexible strip member, said two guide grooves each being closed-off by said cover plate when the latter is connected to said base plate.

3. A device as defined in claim 2, wherein said base plate is provided with a further groove which extends substantially perpendicularly to each of said two guide grooves and which is disposed in the vicinity of said spigot, said further groove being arranged to act as bearing means for a pin provided to facilitate adjustment of said flexible strip member during attachment of said fastening means to the breast bone of such a patient.

4. A device for use in the surgical treatment of a patient suffering from a funnel breast condition, the device comprising in combination: two mutually symmetrical clamping members each having on end portion adapted to be secured to a respective rib of such a patient; fastening means releasably rigidly connecting to one another the respective other end portions of said two clamping members; a fastening element releasably engaging with said fastening means and adapted to attach the latter to the breast bone of such a patient; each clamping member comprising an elongate strip, one surface of said strip being provided with a plurality of depressions equally spaced in the longitudinal direction of the strip and the respective other surface of said strip being provided with a plurality of protrusions complementary with said depressions, said depressions and protrusions provided on said two clamping members being of identical shape; said fastening means comprising a base plate and a cover plate releasably connected to said base plate, said base plate defining a guide groove adapted to receive at least one of said clamping members, a portion of said base plate defining the floor of said guide groove being provided with a plurality of bore holes which, upon said cover plate being connected to said base plate to close said fastening means, engage with said protrusions on a respective one of said stamping members disposed next adjacent said floor of said guide groove, said depressions on said one clamping member being engaged by said protrusions on the respective other said clamping member, which is being retained in engagement with said one clamping member by said cover plate.

5. A device for use in the surgical treatment of a patient suffering from a funnel breast condition, the device comprising in combination: two mutually symmetrical clamping members each having an end portion adapted to be secured to a respective rib of such a patient; fastening means releasably rigidly connecting to one another the respective other end portions of said two clamping members; a fastening element releasably engaging with said fastening means and adapted to attach the latter to the breast bone of such a patient; said fastening means comprising two plate members, one of said plate members being of substantially C-shaped cross-section to define a guide channel adapted to receive the respective other one of said plate members; said base plate being provided, at at least one of the edge portions of said base plate extending substantially parallel to said guide groove therein, with at least one plastically flexible tongue portion, and said cover plate being provided, in at least one edge portion thereof facing the respective said tongue portion, with at least one recess adapted to receive a respective tongue portion of said base plate.

6. A device for use in the surgical treatment of a patient suffering from a funnel breast condition, the device comprising in combination: two mutually symmetrical clamping members each having an end portion adapted to be secured to a respective rib of such a patient; fastening means releasably rigidly connecting to one another the respective other end portions of said two clamping members; a fastening element releasably engaging with said fastening means and adapted to attach the latter to the breast bone of such a patient; said fastening means comprising two plate members, one of said plate members being of substantially C-shaped cross-section to define a guide channel adapted to receive the respective other one of said plate members; said cover plate being provided, at at least one of the edge portions of the cover plate extending substantially parallel to said guide groove in said base plate, with at least one plastically flexible tongue portion, and said base plate being provided, in at least one edge portion thereof facing the respective said tongue portion, with at least one recess adapted to receive a respective said tongue portion of said cover plate.

* * * * *

UNITED STATES PATENT OFFICE
CERTIFICATE OF CORRECTION

Patent No. 3,946,728  Dated March 30, 1976

Inventor(s) Marcel Bettex

It is certified that error appears in the above-identified patent and that said Letters Patent are hereby corrected as shown below:

On the Cover Sheet, item [30] should read as follows:

-- Foreign Application Priority Data

May 28, 1973    Switzerland.........7633

May 15, 1974    Switzerland.........6626/74

Signed and Sealed this

Fourteenth Day of September 1976

[SEAL]

Attest:

RUTH C. MASON
*Attesting Officer*

C. MARSHALL DANN
*Commissioner of Patents and Trademarks*